United States Patent [19]

Fischer, deceased et al.

[11] 4,008,249

[45] Feb. 15, 1977

[54] SUBSTITUTED PYRAZOLES

[75] Inventors: Adolf Fischer, deceased, late of Mutterstadt, Germany, by Caecilia Emma Fischer, heiress-at-law; Rudolf Kropp, Limburgerhof, Germany; Franz Reicheneder, deceased, late of Ludwigshafen, Germany, by Dora Irmgard Reicheneder, heiress-at-law

[73] Assignee: BASF Aktiengesellschaft, Ludwigshafen (Rhine), Germany

[22] Filed: Feb. 27, 1975

[21] Appl. No.: 553,496

[30] Foreign Application Priority Data

Mar. 1, 1974 Germany ........................ 2409775

[52] U.S. Cl. .............................. 260/310 R; 71/92
[51] Int. Cl.$^2$ ................. C07D 231/18; A01N 9/22
[58] Field of Search .............................. 260/310 R

[56] References Cited

OTHER PUBLICATIONS

Chemical Abstracts, vol. 50, pp. 12029–12030 (1956) citing Sandstrom, "Arkiv Kemi" 8, 523–544 (1955) not currently available.

Chemical Abstracts, vol. 56, pp. 11593–11594 (1962) citing Sandstrom "Arkiv Kemi" 15, 195–210 (1960) not currently available in Library.

Chemical Abstracts, vol. 58; item 4540c and vol. 54: pp. 3386f–3387d (1960).

Primary Examiner—Donald B. Moyer
Attorney, Agent, or Firm—Johnston, Keil, Thompson & Shurtleff

[57] ABSTRACT

New and valuable substituted pyrazoles, herbicides containing these compounds as active ingredients, and a process for controlling the growth of unwanted plants with these compounds.

9 Claims, No Drawings

SUBSTITUTED PYRAZOLES

The present invention relates to new and valuable substituted pyrazoles, herbicides containing them, and their use as herbicides.

It is known (German Laid-Open Application DOS 2,260,485) to use 1,2-dimethyl-3,5-diphenyl-pyrazolium methyl sulfate as herbicide. However, its action is poor.

We have now found that substituted pyrazoles of the formula

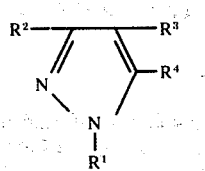

where $R^1$ denotes hydrogen, alkyl, cycloalkyl, aralkyl, substituted or unsubstituted phenyl, or acyl of the formula

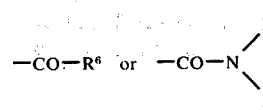

$R^6$ denoting hydrogen, substituted or unsubstituted alkyl, alkoxy, phenoxy or phenyl, and $R^7$ and $R^8$ being identical or different and each denoting hydrogen, alkyl, or substituted or unsubstituted phenyl or alkynyl, $R^2$ denotes substituted or unsubstituted alkyl, cycloalkyl, substituted or unsubstituted phenyl, or a heterocyclic radical having oxygen, nitrogen or sulfur atoms in the ring, $R^3$ denotes hydrogen, chloro, bromo, or lower alkyl, and $R^4$ denotes the radicals $-S-R^5$, $-SO-R^5$ or $-SO_2-R^5$, $R^5$ denoting alkyl, cycloalkyl, aralkyl, substituted or unsubstituted phenyl, or a heterocyclic radical having oxygen, nitrogen or sulfur atoms in the ring, are valuable herbicidally active compounds.

Preferred compounds are those in whose formulae $R^1$ is hydrogen, methyl, ethyl, propyl, isopropyl, n-butyl, isobutyl, sec-butyl, tert-butyl, cyclohexyl, benzyl, phenyl, 2-chlorophenyl, 2-fluorophenyl, 4-fluorophenyl, 3-trifluoromethylphenyl, 4-trifluoromethylphenyl, 4-chlorophenyl, 4-bromophenyl, 3-methylphenyl, 4-methylphenyl, 3,4-dichlorophenyl, 3,5-dichlorophenyl, 2-methyl-4-chlorophenyl, 3-chloro-4-methoxyphenyl, and -COR$^6$ and

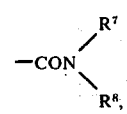

$R^6$ denoting hydrogen, methyl, ethyl, propyl, isopropyl, chloromethyl, dibromomethyl, trichloromethyl, 4-chlorophenoxymethyl, 2,4-dichlorophenoxymethyl, 2,4,5-trichlorophenoxymethyl, 2-methyl-4-chlorophenoxymethyl, 2,4-dichlorophenoxypropyl, methoxy, ethoxy and phenoxy, and $R^7$ and $R^8$ being identical or different and each denoting hydrogen, methyl, ethyl, propyl, isopropyl, isobutyl, phenyl, 3-chlorophenyl, 2,4-dimethylphenyl, 4-fluorophenyl, 3-trifluoromethylphenyl, 4-trifluoromethylphenyl, 2,4-dichlorophenyl, 3,4-dichlorophenyl, 3,5-dichlorophenyl and 3-chloro-4-methoxyphenyl; $R^2$ is ethyl, propyl, isopropyl, chloromethyl, dibromomethyl, trifluoromethyl, α,α-dichloropropyl, cyclohexyl, cyclopentyl, phenyl, 2-chlorophenyl, 2-fluorophenyl, 4-bromophenyl, 4-fluorophenyl, 2,4-dichlorophenyl, 2,6-dichlorophenyl, 3,5-dichlorophenyl, 2-methyl-4-chlorophenyl, 3-methylphenyl, 2,4-dimethylphenyl, 3,5-dimethylphenyl, 3-chloro-4-methoxyphenyl, thienyl-(2) and 2,5-dimethylfuranyl-(3); $R^3$ is hydrogen, chloro, bromo, methyl, ethyl, propyl and isopropyl; and $R^5$ is methyl, ethyl, propyl, isopropyl, dodecyl, cyclohexyl, benzyl, phenylethyl, 4-chlorobenzyl, phenyl, 4-chlorophenyl, 4-fluorophenyl, 4-methoxyphenyl, benzothiazolyl-(2), benzimidazolyl-(2) and pyrimidyl-(2).

The new compounds may be prepared for instance by reacting a substituted vinyl ketone of the general formula

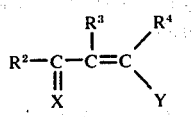

with a hydrazine of the formula

$R^1$ to $R^4$ having the above meanings, X denoting oxygen or sulfur and Y denoting halogen or $R^4$.

The compounds may also be prepared by reacting a 5-halopyrazole of the general formula

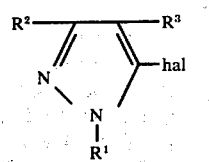

with a mercaptan of the general formula

$R^1$, $R^2$, $R^3$ and $R^5$ having the preferred meanings and hal denoting chloro, bromo and iodo.

The route employing hydrazine and its derivatives is preferred.

The 5-halopyrazoles may be produced for instance by halogenating a 5-unsubstituted pyrazole, e.g., with bromine in glacial acetic acid.

Pyrazoles in which $R^4$ is $-SOR^5$ and $-SO_2R^5$ may be prepared by oxidizing pyrazoles of the general formula

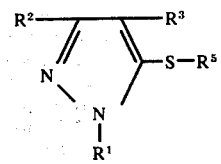

$R^1$, $R^2$, $R^3$ and $R^5$ having the above meanings.

Finally, pyrazoles in which the hydrogen is replaced in the 1-position by alkyl, benzyl, -COR$^6$ or

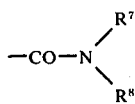

may be prepared by reacting pyrazoles of the general formula

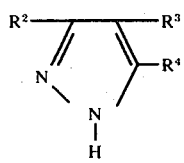

with alkylating agents, acid chlorides, acid anhydrided or isocyanates. $R^2$, $R^3$, $R^4$, $R^6$, and $R^8$ have the above meanings.

The preparation of the compounds of the invention is illustrated by the following examples.

EXAMPLE 1

70 parts (by weight) of β,β-di-(phenylthio)-vinyl phenyl ketone (A. E. Pohland and W. R. Benson, Chem. Rev., 66, 161 to 197, 1966) is mixed with 700 parts of dioxane and 20 parts of hydrazine hydrate for 3 hours at 90° to 100° C. After the dioxane has been distilled off, the oil which remains is mixed with 200 parts of a 10 wt% aqueous caustic solution. There is obtained 46 parts (91% of theory) of 3-phenyl-5-phenylthiopyrazole. After recrystallization from cyclohexane the compound melts at 99° to 100° C.

EXAMPLE 2

280 parts of β-chloro-β-(phenylthio)-vinyl phenyl ketone (A. G. Gudkova, Izv. Akad. SSSR, 1248 to 1254, 1962) is mixed with 55 parts of hydrazine hydrate and 42 parts of sodium hydroxide in 1,200 parts of methanol for 3 hours at 60° to 65° C. After 1,000 parts of water has been added, 240 parts (95.3% of theory) of 3-phenyl-5-phenylthiopyrazole is obtained; m.p.: 99° to 100° C (from cyclohexane).

EXAMPLE 3

13.7 parts of β-chloro-β-(phenylthio)-vinyl phenyl ketone is boiled for 3 hours with 5 parts of methyl hydrazine in 150 parts of dioxane. After the dioxane has been distilled off and 100 parts of water added to the residue there is obtained 11.5 parts (86.5% of theory) of 1-methyl-3-phenyl-5-phenylthiopyrazole. After recrystallization from ligroin, the compound melts at 61° to 62° C.

EXAMPLE 4

At 20° to 25° C, a few drops of concentrated sulfuric acid are added to a solution of 10 parts of 3-phenyl-5-phenylthiopyrazole in 100 parts of acetic anhydride. After 15 hours the solution is concentrated in vacuo and 50 parts of water is added to the residue. There is obtained 10.5 parts (90% of theory) of 1-acetyl-3-phenyl-5-phenylthiopyrazole; m.p.: 83° to 84.5° C (recrystallized from methanol).

EXAMPLE 5

Over a period of 30 minutes, a solution of 12.6 parts of 3-phenyl-5-phenylthiopyrazole in 50 parts of chloroform is added to a mixture of 20 parts of m-chlorobenzoic peracid (85%) in 150 parts of chloroform, the temperature rising from 25° to 40° C. The reaction solution is stirred with 20 parts of sodium bicarbonate slurried in 200 parts of water. The deacidified chloroform solution is separated and concentrated. There is obtained 13 parts (91.5% of theory) of 3-phenyl-5-phenylsulfone pyrazole; m.p.: 172° to 174° C (recrystallization from methanol).

EXAMPLE 6

At 25° C, 8 parts of bromine is slowly added, with stirring, to a solution of 12.6 parts of 3-phenyl-5-phenylthiopyrazole in 150 parts of glacial acetic acid. After 12 hours, the solution is concentrated in vacuo and the residue treated with about 50 parts of water. There is obtained 16 parts (96.7% of theory) of 3-phenyl-4-bromo-5-phenylthiopyrazole; m.p.: 121° to 122° C (recrystallized from cyclohexane).

EXAMPLE 7

12.6 parts of 3-phenyl-5-phenylthiopyrazole, 100 parts of toluene and 6 parts of phenyl isocyanate are stirred for 12 hours at 20° C. After the toluene has been distilled off, there is obtained 13 parts (70% of theory) of 1-(phenylcarbamoyl)-3-phenyl-5-phenylthiopyrazole; m.p.: 138° to 139.5° C (recrystallized from acetonitrile).

The following compounds were prepared analogously:

| Compound | | |
|---|---|---|
| 3-phenyl-5-methylthiopyrazole | m.p. | 76° to 77° C |
| 3-phenyl-5-dodecylthiopyrazole | m.p. | 45.5° to 46.5° C |
| 3-phenyl-5-benzylthiopyrazole | m.p. | 84.5° to 86° C |
| 3-phenyl-5-p-chlorophenylthiopyrazole | m.p. | 159° to 160° C |
| 3-phenyl-5-phenylsulfoxypyrazole | m.p. | 175° to 177° C |
| 3-p-chlorophenyl-5-phenylthiopyrazole | m.p. | 128° to 129.5° C |
| 3-p-bromophenyl-5-phenylthiopyrazole | m.p. | 140° to 141° C |
| 3-(2,4-dichlorophenyl)-5-phenylthiopyrazole | m.p. | 87° to 89° C |
| 3-m-tolyl-5-phenylthiopyrazole | m.p. | 148° to 149° C |
| 3-(3,5-dimethylphenyl)-5-phenylthiopyrazole | m.p. | 93° to 94° C |
| 1,3-diphenyl-5-phenylthiopyrazole | oil, | $n_D^{20}$: 1.6301 |
| 1-benzyl-3-phenyl-5-phenylthiopyrazole | m.p. | 76° to 77° C |
| 3-cyclohexyl-5-phenylthiopyrazole | m.p. | 93° to 94° C |
| 3-isopropyl-5-phenylthiopyrazole | m.p. | 75° to 76° C |
| 3-(2-thienyl)-5-phenylthiopyrazole | m.p. | 94° to 95° C |
| 1-benzoyl-3-phenyl-5-phenylthiopyrazole | m.p. | 101° to 102° C |
| 1-[α-(2,4-dichlorophenoxy)-propionyl]-3-phenyl-5-phenylthiopyrazole | m.p. | 107.5° C to 108.5° C |
| 1-carbethoxy-3-phenyl-5-phenylthiopyrazole | m.p. | 104.5° to 105.5° C |
| 1-(methylcarbamoyl)-3-phenyl-5-phenylthiopyrazole | m.p. | 91° to 92° C |

| -continued | |
|---|---|
| 3-phenyl-5-(2-benzothiazolyl)-thiopyrazole | m.p. 143° to 144° C |

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as

| | |
|---|---|
| Cynodon spp. | Dactylis spp. |
| Digitaria spp. | Avena spp. |
| Echinochloa spp. | Bromus spp. |
| Setaria spp. | Uniola spp. |
| Panicum spp. | Poa spp. |
| Alopercurus spp. | Leptochloa spp. |
| Lolium spp. | Brachiaria spp. |
| Sorghum spp. | Eleusine spp. |
| Agropyron spp. | Cenchrus spp. |
| Phalaris spp. | Eragrostis spp. |
| Apera spp. | Phragmites communis |
| etc.; | |
| Cyperaceae, such as | |
| Carex spp. | Eleocharis spp. |
| Cyperus spp. | Scirpus spp. |
| etc.; | |
| dicotyledonous weeds, such as | |
| Malvaceae, e.g., | |
| Abutilon theoprasti | |
| Sida spp. | Hibiscus spp. |
| etc.; | Malva spp. |
| Compositae, such as | |
| Ambrosia spp. | Centaurea spp. |
| Lactuca spp. | Tussilago spp. |
| Senecio spp. | Lapsana communis |
| Sonchus spp. | Tagetes spp. |
| Xanthium spp. | Erigeron spp. |
| Iva spp. | Anthemis spp. |
| Galinsoga spp. | Matricaria spp. |
| Taraxacum spp. | Artemisia spp. |
| Chrysanthemum spp. | Bidens spp. |
| Cirsium spp. | etc.; |
| Convolvulaceae, such as | |
| Convolvulus spp. | Cuscuta spp. |
| Ipomoea spp. | Jaquemontia tamnifolia |
| etc.; | |
| Cruciferae, such as | |
| Barbarea vulgaris | Arabidopsis thaliana |
| Brassica spp. | Descurainia spp. |
| Capsella spp. | Draba spp. |
| Sisymbrium spp. | Coronopus didymus |
| Thlaspi spp. | Lepidium spp. |
| Sinapis arvensis | Raphanus spp. |
| etc.; | |
| Geraniaceae, such as | |
| Erodium spp. | Geranium spp. |
| etc.; | |
| Portulacaceae, such as | |
| Portulaca spp. | etc.; |
| Primulaceae, such as | |
| Anagallis arvensis | Lysimachia spp. |
| etc.; | |
| Rubiaceae, such as | |
| Richardia spp. | Diodia spp. |
| Galium spp. | etc.; |
| Scrophulariaceae, such as | |
| Linaria spp. | Digitalis spp. |
| Veronica spp. | etc.; |
| Solanaceae, such as | |
| Physalis spp. | Nicandra spp. |
| Solanum spp. | Datura spp. |
| etc.; | |
| Urticaceae, such as | |
| Urtica spp. | |
| Violaceae, such as | |
| Viola spp. | etc.; |
| Zygophyllaceae, such as | |
| Tribulus terrestris | etc.; |
| Euphorbiaceae, such as | |

| -continued | |
|---|---|
| Mercurialis annua | Euphorbia spp. |
| Umbelliferae, such as | |
| Daucus carota | Ammi majus |
| Aethusa cynapium | etc.; |
| Commelinaceae, such as | |
| Commelina spp. | etc.; |
| Labiatae, such as | |
| Lamium spp. | Galeopsis spp. |
| etc.; | |
| Leguminosae, such as | |
| Medicago spp. | Sesbania exaltata |
| Trifolium spp. | Cassia spp. |
| Vicia spp. | Lathyrus spp. |
| etc.; | |
| Plantaginaceae, such as | |
| Plantago spp. | etc.; |
| Polygonaceae, such as | |
| Polygonum spp. | Fagopyrum spp. |
| Rumex spp. | etc.; |
| Aizoaceae, such as | |
| Mollugo verticillata | etc.; |
| Amaranthaceae, such as | |
| Amaranthus spp. | etc.; |
| Boraginaceae, such as | |
| Amsinckia spp. | Anchusa spp. |
| Myostis spp. | Lithospermum spp. |
| etc.; | |
| Caryophyllaceae, such as | |
| Stellaria spp. | Silene spp. |
| Spergula spp. | Cerastium spp. |
| Saponaria spp. | Agrostemma githago |
| Scleranthus annuus | etc.; |
| Chenopodiaceae, such as | |
| Chenopodium spp. | Atriplex spp. |
| Kochia spp. | Monolepsis nuttalliana |
| Salsola Kali | etc.; |
| Lythraceae, such as | |
| Cuphea spp. | etc.; |
| Oxalidaceae, such as | |
| Oxalis spp. | |
| Ranunculaceae, such as | |
| Ranunculus spp. | Adonis spp. |
| Delphinium spp. | etc.; |
| Papaveraceae, such as | |
| Papaver spp. | Fumaria officinalis |
| etc.; | |
| Onagraceae, such as | |
| Jussiaea spp. | etc.; |
| Rosaceae, such as | |
| Alchemillia spp. | Potentilla spp. |
| etc.; | |
| Potamogetonaceae, such as | |
| Potamogeton spp. | etc.; |
| Najadaceae, such as | |
| Najas spp. | etc.; |
| Equisetaceae | |
| Equisatum spp. | etc.; |
| Marsileaceae, such as | |
| Marsilea quadrifolia | etc.; |
| Polypodiaceae, | |
| Pteridium quilinum | |
| Alismataceae, such as | |
| Alisma spp. | Sagittaria sagittifolia |
| etc. | |

The herbicides according to the invention may be employed in cereal crops such as

| | |
|---|---|
| Avena spp. | Sorghum |
| Triticum spp. | Zea mays |
| Hordeum spp. | Panicum miliaceum |
| Secale spp. | Oryza spp. |
| Saccharum offinicarum | |
| and in dicotyledon crops such as | |
| Cruciferae, e.g. | |
| Brassica spp. | Raphanus spp. |
| Sinapis spp. | Lepidium spp. |
| Compositae, e.g. | |
| Lactuca spp. | Carthamus spp. |
| Helianthus spp. | Scorzonera spp. |
| Malvaceae, e.g. | |
| Gossypium hirsutum | |

-continued

| | |
|---|---|
| Leguminosae, e.g. | |
| Medicago spp. | Phaseolus spp. |
| Trifolium spp. | Arachis spp. |
| Pisum spp. | Glycine max. |
| Chenopodiaceae, e.g. | |
| Beta vulgaris | |
| Spinacia spp. | |
| Solanaceae, e.g. | |
| Solanum spp. | Capsicum annuum |
| Nicotiania spp. | |
| Linaceae, e.g. | |
| Linum spp. | |
| Umbelliferae, e.g. | |
| Petroselinum spp. | Apium graveolens |
| Daucus carota | |
| Rosaceae, e.g. | Fragaria |
| Cucurbitaceae, e.g. | |
| Cucumis spp. | Cucurbita spp. |
| Liliaceae, e.g. | |
| Allium spp. | |
| Vitaceae, e.g. | |
| Vitis vinifera | |
| Bromeliaceae, e.g. | |
| Ananas sativus. | |

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or aninmal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ether, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestome, lime, chalk, bole, loess, clay, dolomite, diatomaceous earth, calcium sulfate, magnesium oxide, ground plastics, fertilizers, such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tankmix) ) oils of various types, herbicides, fungicides nematocides, insecticides, bactericides, trace elements, fertilizers, antifoams (e.g., silicones), growth regulators, antidotes and other herbicidally effective compounds such as
substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphoric acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

EXAMPLE 8

In the greenhouse, various plants were treated at a growth height of from 6 to 18 cm with 0.75 kg/ha of each of the following active ingredients, each being dispersed or emulsified in 500 liters of water per hectare:

I 3-phenyl-5-phenylthiopyrazole
II 3-phenyl-5-benzylthiopyrazole
III 1-acetyl-3-phenyl-5-phenylthiopyrazole and, for comparison purposes,
IV 1,2-dimethyl-3,5-diphenylpyrazolium methyl sulfate.

After 2 to 3 weeks it was ascertained that active ingredients I, II and III had a better herbicidal action than compound IV, combined with the same crop plant compatability.

The results are given below:

| Active ingredient kg/ha | I 0.75 | II 0.75 | III 0.75 | IV 0.75 |
|---|---|---|---|---|
| Crop plants: | | | | |
| Triticum aestivum | 0 | 0 | 0 | 0 |
| Hordeum vulgare | 0 | 0 | 0 | 0 |
| Beta vulgaris | 0 | 0 | 0 | 0 |
| Brassica napus | 0 | 0 | 0 | 0 |
| Unwanted plants: | | | | |
| Alopecurus myosuroides | 80 | 70 | 75 | 40 |
| Avena fatua | 90 | 70 | 80 | 30 |
| Lolium multiflorum | 70 | 50 | 60 | 10 |
| Poa annua | 80 | 60 | 70 | 20 |

0 = no damage, 100 = complete destruction

EXAMPLE 9

In the greenhouse, loamy sandy soil was filled into pots and sown with the seeds of various plants. The soil prepared in this manner was then immediately treated with 2 kg/ha of each of the following active ingredients, each being dispersed or emulsified in 500 liters of water per hectare:

I 3-phenyl-5-phenylthiopyrazole
II 3-phenyl-5-benzylthiopyrazole
III 1-acetyl-3-phenyl-5-phenylthiopyrazole and, for comparison purposes,
IV 1,2-dimethyl-3,5-diphenylpyrazolium methyl sulfate.

After 3 to 4 weeks it was ascertained that active ingredients I, II and III had a better herbicidal action than compound IV, combined with the same crop plant compatibility.

The results are given below:

| Active ingredient kg/ha | I 2.0 | II 2.0 | III 2.0 | IV 2.0 |
|---|---|---|---|---|
| Crop plants: | | | | |
| Triticum aestivum | 5 | 5 | 5 | 5 |
| Hordeum vulgare | 0 | 0 | 0 | 0 |
| Beta vulgaris | 0 | 0 | 0 | 0 |
| Brassica napus | 0 | 0 | 0 | 0 |
| Unwanted plants: | | | | |
| Alopecurus myosuroides | 90 | 60 | 60 | 20 |
| Lolium multiflorum | 100 | 70 | 75 | 10 |
| Lolium perenne | 90 | 70 | 70 | 10 |
| Poa annua | 100 | 80 | 75 | 20 |
| Echinochloa crus-galli | 90 | — | 90 | 10 |

| Active ingredient kg/ha | I 2.0 | II 2.0 | III 2.0 | IV 2.0 |
|---|---|---|---|---|

0 = no damage
100 = complete destruction

EXAMPLE 10

90 parts by weight of compound I is mixed with 10 parts by weight of N-methyl-α-pyrrolidone. A mixture is obtained which is suitable for application in the form of very fine drops.

EXAMPLE 11

20 parts by weight of compound I is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 12

20 parts by weight of compound I is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 13

20 parts of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 14

20 parts by weight of the compound of Example 3 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 15

3 parts by weight of compound I is intimately mixed with 97 parts by weight of particulate kaolin. A dust is obtained containing 3% by weight of the active ingredient.

EXAMPLE 16

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 17

In the greenhouse, various plants were treated at a growth height of from 5 to 16 cm with the following active ingredients I 3-(3',5'-dimethylphenyl)-5-phenylthiopyrazole, 0.75 kg/ha + 2 l/ha of the adduct of 6 to 7 moles of ethylene oxide to 1 mole of isooctylphenol II 1-[α-(2,4-dichlorophenoxy)-propionyl]-3-phenylthiopyrazole, 0.75 kg/ha + 2 l/ha of the adduct of 6 to 7 moles of ethylene oxide to 1 mole of isooctylphenyl.

Each composition was dispersed or emulsified in 500 liters of water per hectare.

After 2 to 3 weeks it was ascertained that active ingredients I and II had a good herbicidal action and good crop plant compatability.

The results are given below:

| Active ingredient kg/ha | I 0.75+2.0 | II 0.75+2.0 |
|---|---|---|
| Crop plants: | | |
| Triticum aestivum | 0 | 0 |
| Hordeum vulgare | 0 | 0 |
| Secale cereale | 0 | 0 |
| Beta vulgaris | 0 | 0 |
| Unwanted plants: | | |
| Avena fatua | 80 | 80 |
| Sinapis arvensis | 70 | 90 |

0 = no damage
100 = complete destruction

EXAMPLE 18

In the greenhouse, loamy sandy soil was filled into pots and sown with various seeds. The soil was then immediately treated with 2 kg/ha of each of the following active ingredients, each being dispersed or emulsified in 500 liters of water per hectare:

I 3-(,5'-dimethylphenyl)-5-phenylthiopyrazole

II 1-[α(2,4-dichlorophenoxy)-propionyl]-3-phenyl-5-phenylthiopyrazole.

After 4 to 5 weeks it was ascertained that active ingredients I and II had a good herbicidal action and good crop plant compatibility.

The results are given below:

| Active ingredient kg/ha | I 2 | II 2 |
|---|---|---|
| Crop plants: | | |
| Triticum aestivum | 5 | 5 |
| Hordeum vulgare | 5 | 5 |
| Beta vulgaris | 0 | 0 |
| Unwanted plants: | | |
| Echinochloa crus-galli | 50 | 90 |
| Lolium multiflorum | 60 | 80 |
| Sinapis arvensis | 80 | 90 |

0 = no damage
100 = complete destruction

The action of the following compounds corresponds to that of those in Examples 17 and 18:

3-phenyl-5-methylthiopyrazole
3-isopropyl-5-phenylthiopyrazole
3-cyclohexyl-5-phenylthiopyrazole
3-thiophenyl-5-phenylthiopyrazole
1-benzyl-3-phenyl-5-phenylthiopyrazole
1-phenyl-3-phenyl-5-phenylthiopyrazole
1-benzoyl-3-phenyl-5-phenylthiopyrazole
1-(N-methylcarbamoyl)-3-phenyl-5-phenylthiopyrazole
1-(N-phenylcarbamoyl)-3-phenyl-5-phenylthiopyrazole

We claim:

1. A substituted pyrazole of the formula:

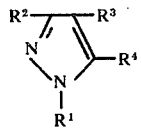

in which $R^1$ denotes hydrogen, methyl, ethyl, propyl, isopropyl, n-butyl, isobutyl, sec-butyl, tert-butyl, cyclohexyl, benzyl, phenyl, 2-chlorophenyl, 2-fluorophenyl, 4-fluorophenyl, 3-trifluoromethylphenyl, 4-trifluoromethylphenyl, 4-chlorophenyl, 4-bromophenyl, 3-methylphenyl, 4-mehtylphenyl, 3,4-dichlorophenyl, 3,5-dichlorophenyl, 2-methyl-4-chloro phenyl, or 3-chloro-4-methoxphenyl, or $R^1$ denotes -$COR^6$ in which $R^6$ denotes hydrogen, methyl, ethyl, propyl, isopropyl, chloromethyl, dibromoethyl, trichloromethyl, 4-chlorophenoxymethyl, 2,4-dichlorophenoxymehtyl, 2,4,5-trichlorophenoxymethyl, 2-methyl-4-chlorophenoxymethyl, 2,4-dichlorophenoxypropyl, methoxy, ethoxy or phenoxy; or $R^1$ denotes

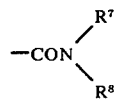

wherein $R^7$ and $R^8$ are identical or different and each denotes hydrogen, methyl, ethyl, propyl, isopropyl, isobutynyl, phenyl, 3-chlorophenyl, 2,4-dimethylphenyl, 4-fluorophenyl, 3-trifluoromethylphenyl, 4-trifluoromethylphenyl, 2,4-dichlorophenyl, 3,4-dichlorophenyl, 3,5-dichlorophenyl and 3-chloro-4-methoxyphenyl;

$R^2$ denotes phenyl, 2-chlorophenyl, 2-fluorophenyl, 4-bromophenyl, 4-fluorophenyl, 2,4-dichlorophenyl, 2,6-dichlorophenyl, 3,5-dichlorophenyl, 2-methyl-4-chlorophenyl, 3-methylphenyl, 2,4-dimethylphenyl, 3,5-dimethylphenyl, or 3-chloro-4-methoxyphenyl; $R^3$ denotes hydrogen, chloro, bromo, methyl, ethyl, propyl or isopropyl; and $R^4$ denotes -S-$R^5$, in which $R^5$ denotes phenyl.

2. A substituted pyrazole as claimed in claim 1 wherein $R^1$ denotes hydrogen, and $R^3$ denotes hydrogen.

3. A substituted pyrazole as claimed in claim 1 wherein $R^1$ denotes -$COR^6$ and $R^3$ denotes hydrogen.

4. A substituted pyrazole of the formula

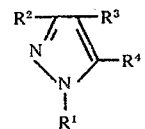

in which $R^1$ denotes hydrogen, methyl, ethyl, propyl, isopropyl, n-butyl, isobutyl, sec-butyl, tert-butyl, cyclohexyl, benzyl, phenyl, 2-chlorophenyl, 2-fluorophenyl, 4-fluorophenyi, 3-trifluoromethylphenyl, 4-trifluoromethylphenyl, 4-chlorophenyl, 4-bromophenyl, 3-methylphenyl, 4-methylphenyl, 3,4-dichlorophenyl, 3,5-dichlorophenyl, 2-methyl-4-chlorophenyl or 3-chloro-4-methoxyphenyl; $R^2$ denotes phenyl, 2-chlorophenyl, 2-fluorophenyl, 4-bromophenyl, 4-fluorophenyl, 2,4-dichlorophenyl, 2,6-dichlorophenyl, 3,5-dichlorophenyl, 2-methyl-4-chlorophenyl, 3-methylphenyl, 2,4-dimethylphenyl, 3,5-dimethylphenyl, or 3-chloro-4-methoxyphenyl;

$R^3$ denotes hydrogen; and $R^4$ denotes -S-$R^5$, in which $R^5$ denotes phenyl.

5. 3-phenyl-5-phenylthiopyrazole.
6. 3-phenyl-5-benzylthiopyrazole.
7. 1-acetyl-3-phenyl-5-phenylthiopyrazole.
8. 3-(3',5'-dimethylphenyl)-5-phenylthiopyrazole.
9. 1-[α-(2,4-dichlorophenoxy)-propionyl]-3-phenyl-5-phenylthiopyrazole.

* * * * *

UNITED STATES PATENT AND TRADEMARK OFFICE
CERTIFICATE OF CORRECTION

PATENT NO. : 4,008,249

DATED : February 15, 1977

INVENTOR(S) : Adolf Fischer, deceased et al.

It is certified that error appears in the above-identified patent and that said Letters Patent are hereby corrected as shown below:

In the Heading, under "Foreign Application Priority Data"
delete " Mar. 1, 1974  Germany ................ 2409775"
and substitute -- Mar. 1, 1974  Germany .......... 2409753 --

Signed and Sealed this

First Day of November 1977

[SEAL]

Attest:

RUTH C. MASON
Attesting Officer

LUTRELLE F. PARKER
Acting Commissioner of Patents and Trademarks